US008507694B2

(12) United States Patent
Gribkov et al.

(10) Patent No.: US 8,507,694 B2
(45) Date of Patent: Aug. 13, 2013

(54) PROCESS FOR THE PREPARATION OF PYRAZOLE CARBOXYLIC ACID AMIDES

(75) Inventors: Denis Gribkov, Münchwilen (CH); Adrian Müller, Münchwilen (CH); Martin Lager, Münchwilen (CH); Fanny Giordano, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/389,000

(22) PCT Filed: Jul. 7, 2010

(86) PCT No.: PCT/EP2010/059703
§ 371 (c)(1),
(2), (4) Date: Feb. 6, 2012

(87) PCT Pub. No.: WO2011/015416
PCT Pub. Date: Feb. 10, 2011

(65) Prior Publication Data

US 2012/0136162 A1 May 31, 2012

(30) Foreign Application Priority Data

Aug. 6, 2009 (EP) .................................... 09167363
Sep. 4, 2009 (EP) .................................... 09169501

(51) Int. Cl.
*C07D 231/14* (2006.01)
*C07C 45/62* (2006.01)
*C07C 49/693* (2006.01)
*C07C 251/44* (2006.01)

(52) U.S. Cl.
USPC ......................... 548/374.1; 564/267; 568/373

(58) Field of Classification Search
None
See application file for complete search history.

(56) References Cited

FOREIGN PATENT DOCUMENTS

| | | |
|---|---|---|
| WO | 2004/035589 | 4/2004 |
| WO | 2007/048556 | 5/2007 |

*Primary Examiner* — Kamal Saeed
(74) *Attorney, Agent, or Firm* — R. Kody Jones

(57) ABSTRACT

The invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide.

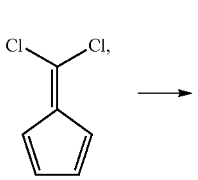

(II)

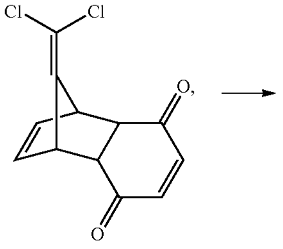

(IV)

-continued

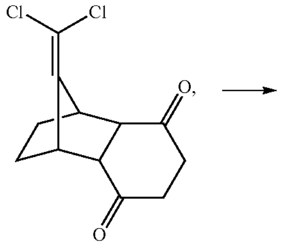

(V)

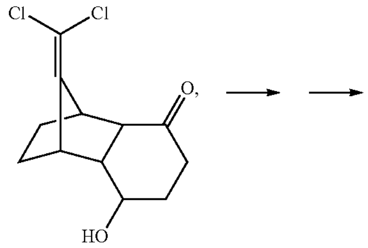

(VI)

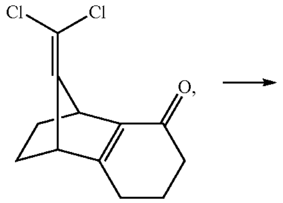

(VII)

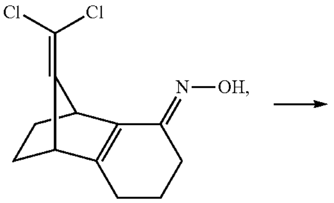

(VIII)

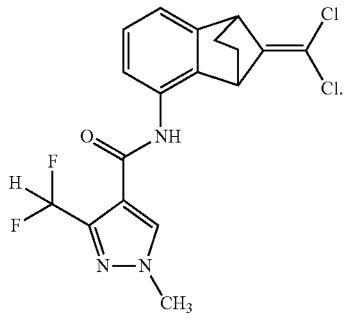

(I)

8 Claims, No Drawings

PROCESS FOR THE PREPARATION OF PYRAZOLE CARBOXYLIC ACID AMIDES

This application is a 371 of International Application No. PCT/EP2010/059703 filed Jul. 7, 2010, which claims priority to EP 09167363.2 filed Aug. 6, 2009, and EP 09169501.5 filed Sep. 4, 2009, the contents of which are incorporated herein by reference.

The present invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide.

The compound 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties is described for example in WO 2007/048556.

The preparation of 3-difluoromethyl-1-methyl-1H-pyrazole-4-carboxylic acid (9-dichloromethylene-1,2,3,4-tetrahydro-1,4-methano-naphthalen-5-yl)-amide is known from WO 2007/048556. Said compound can be prepared according to schemes 1 and 4 by a) reacting the compound of formula A (A)

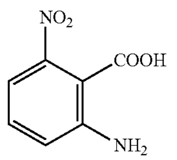

in the presence of an alkyl nitrite with a compound of formula B (B)

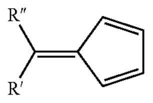

wherein R' and R" are e.g. $C_1$-$C_4$alkyl, to a compound of formula C (C)

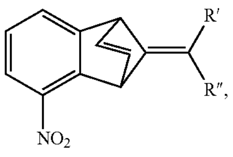

b) hydrogenating the compound of formula C in the presence of a suitable metal catalyst to a compound of formula D (D)

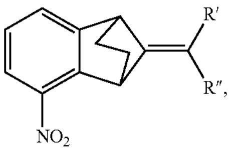

c) ozonising the compound of formula D and subsequent treatment with a reducing agent to a compound of formula E (E)

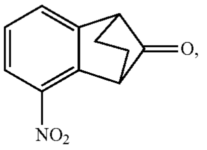

d) reacting the compound of formula E in the presence of triphenylphosphine/carbon tetrachloride to 2,9-dichloromethylidene-5-nitro-benzonorbornene of formula F (F)

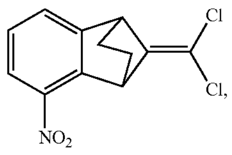

e) hydrogenating the compound of formula F in the presence of a metal catalyst to 2,9-dichloromethylidene-5-amino-benzonorbornene of formula G (G)

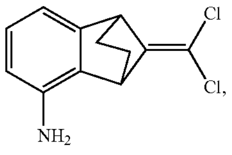

f) and reacting the compound of formula G with a compound of formula H (H)

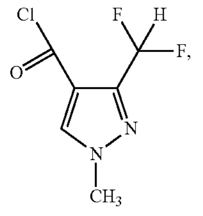

to 3-difluoromethyl-1-methyl-1H-pyrazole-4-carboxylic acid (9-dichloromethylene-1,2,3,4-tetrahydro-1,4-methano-naphthalen-5-yl)-amide.

Significant disadvantages of this prior art process is the ozonolysis reaction which is difficult to handle and the expensive step d) which requires the use of triphenylphosphine. Said disadvantages make this process uneconomic and especially unsuitable for a large-scale production.

The aim of the present invention is therefore to provide a novel process for the production of 3-difluoromethyl-1-methyl-1H-pyrazole-4-carboxylic acid (9-dichloromethylene-1,2,3,4-tetrahydro-1,4-methano-naphthalen-5-yl)-amide that avoids the disadvantages of the known process and makes it possible to prepare 3-difluoromethyl-1-methyl-1H-pyrazole-4-carboxylic acid (9-dichloromethylene-1,2,3,4-tetrahydro-1,4-methano-naphthalen-5-yl)-amide in high yields and good quality in an economically advantageous way.

Thus, according to the present invention, there is provided a process for the preparation of the compound of formula I (I)

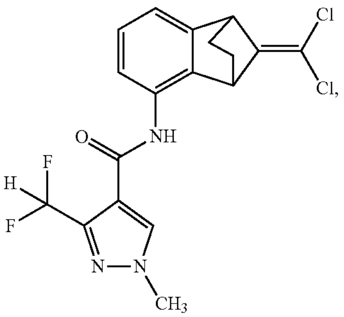

which process comprises a) reacting the compound of formula II (II)

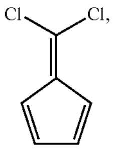

in the presence of a catalyst in a suitable organic solvent with the compound of formula III (III)

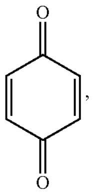

to the compound of formula IV (IV)

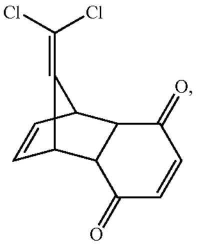

b) hydrogenating the compound of formula IV in the presence of a metal catalyst to the compound of formula V (V)

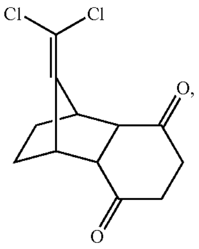

c) reducing the compound of formula V in the presence of a reducing agent to the compound of formula VI (VI)

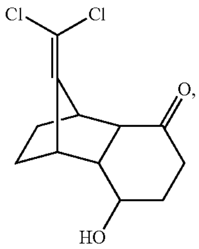

d) dehydrating the compound of formula VI in the presence of an acid to the compound of formula VII (VII)

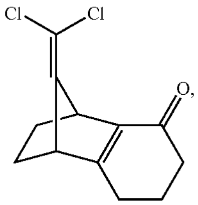

e) reacting the compound of formula VII with hydroxylamine to the compound of formula VIII (VIII)

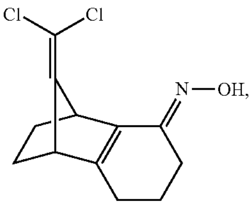

and f) acylating the oxime oxygen of the compound of formula VIII in the presence of a solvent and an acylating agent and finally reacting the obtained product with the compound of formula IX (IX)

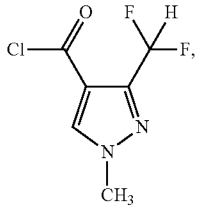

or ff) reacting the compound of formula VIII with an excess of the compound of formula IX.

Reaction Step a):

The compound of formula II is known and disclosed e.g. in Chemical Communications, 20, 1293 (1971). The compound of formula II can be, for example, prepared by reacting cyclopentadiene with $CCl_4$ in the presence of a metal catalyst selected from ruthenium, copper, iron, palladium and rhodium complexes to the compound of formula X (X)

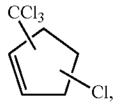

and reacting the compound of formula X with a base in an appropriate solvent to the compound of formula II.

The compound of formula III is known and commercially available.

The compound of formula IV (and its endo and exo isomers) is novel and especially developed for the process according to the invention and therefore constitute a further object of the invention.

Suitable inert organic solvents for reaction step a) are for example toluene, xylene, benzene, methyl cyclohexane, dichloromethane or chlorobenzene, preferably toluene. The reaction can be advantageously performed in the presence of Lewis acids as catalysts. Also some strong Bronsted acids, for example Methansulfonic acid as well as immobilized on solid support Bronsted acids, for example AMBERLYSTs can be used as catalyst. Lewis acids were more efficient than Bronsted acids.

Suitable lewis acids are for example $SnCl_4$, $AlCl_3$ or $FeCl_3$. A donor ligand can be added to increase the yield, especially if $AlCl_3$ or $FeCl_3$ is used as the catalyst. Preferred donor ligands are diethylether, tetrahydrofurane, nitromethane or nitrobenzene. A preferred catalyst for reaction step a) is $AlCl_3$ (advantageously used in an amount of 1-100 mol %, preferred in an amount of 10-20 mol %) in the presence of tetrahydrofurane. Tetrahydrofurane can be added in an amount of 1 to 3 equivalents, in particular in 1.1 equivalents with respect to the used $AlCl_3$. In a preferred embodiment of the invention, said preferred catalyst can be advantageously prepared by the addition of tetrahydrofurane to a suspension of $AlCl_3$ in a solvent (for example in toluene) at −10° C. to 60° C., preferably at 25° C. The $AlCl_3$/tetrahydrofurane solution can be added to the mixture of compounds of formulae II and III in a solvent (for example in toluene) at a temperature of −20° C. to 30° C., preferably −10° C. The $AlCl_3$/diethylether solution can be added to the mixture of compounds of formulae II and III in chlorobenzene at a temperature of −50° C. to −30° C., preferably −35° C. In another preferred embodiment of the invention, solid $AlCl_3$ can be added to the reaction mixture which contains the compounds of formula II and III and tetrahydrofurane or diethylether at temperatures mentioned above.

Reaction Step b):

The compound of formula V and its isomers are novel and especially developed for the process according to the invention and therefore constitute a further object of the invention.

Suitable heterogeneous metal catalysts for reaction step b) are fine dispersed metals of the groups 8, 9 and 10 of the periodic table of elements, optionally on a solid support as for example active carbon, aluminum oxide or calcium oxide, preferably Pd/C, Pt/C, Rh/C or a Nickel (-alloy) sponge catalyst (e.g. Raney-Nickel). With Pd/C, Pt/C and Rh/C the hydrogenation can be advantageously performed at 1000-15000 hPa hydrogen pressure and at 0 to 60° C., preferably at 30-35° C. or ambient temperature, while Raney-Nickel requires higher hydrogen pressure, for example 1000-30000 hPa. A preferred catalyst is Rh/C, in particular with 0.03-0.5 mol % loading and at a hydrogen pressure of 1000-15000 hPa, preferably at a hydrogen pressure of 2000-5000 hPa, in particular at a hydrogen pressure of 3000 hPa. Reaction step b) is performed in the presence of a solvent. Suitable organic solvents for reaction step b) are for alcohols, esters, ethers, optionally chlorinated aromatic and aliphatic hydrocarbons as for example propan-2-ol, pentanol, tetrahydrofurane, toluene, xylene, acetic acid ethylester or tert.butyl-methylether in particular tetrahydrofurane. The hydrogenation reaction can be performed at low to elevated temperatures, preferably at temperatures of from 0 to 80° C., more preferably of from 20 to 60° C., in particular at 30-35° C. The hydrogenation may be also achieved with homogeneous hydrogenation catalysts (Iridium, Rhodium or Ruthenium complexes, for example $(Ph_3P)_3RhCl$), as well as by transfer hydrogenation reaction using e.g. propan-2-ol, cyclohexadiene or diimide (HN═NH) generated in situ.

Reaction Step c):

The compound of formula VI and its isomers are novel and especially developed for the process according to the invention and therefore constitute a further object of the invention. Suitable reducing agents are for example hydrogen with a metal catalyst, $NaBH_4$, monoacetoxyborohydride ($NaBH_3OAc$), $LiAlH_4$, sodium bis(2-methoxyethoxy)aluminum hydride (Red-Al), diisobutylaluminium hydride (DIBAL-H) or borane ($BH_3$*$SMe_2$, $BH_3$*tetrahydrofurane) or a transfer hydrogenation from formate or alcohol. Especially preferred is $NaBH_4$. Reduction step c) can, in some cases, also be performed in presence of the hydrogenation catalyst used for reaction step b). Reduction with $NaBH_4$ is advantageously performed in a solvent or mixtures of solvents, e.g. in an alcohol, for example in methanol, ethanol, isopropanol, tetrahydrofurane/methanol mixture, tetrahydrofurane/ethanol mixture, preferably in methanol/tetrahydrofurane. Preferred temperatures are −20 to +40° C., in particular 0-30° C. It is also possible to use hydrogen in the presence of a catalyst as reducing agent.

Reaction Step d):

Suitable acids for reaction step d) are strong acids like phosphoric acid, polyphosphoric acids, concentrated $H_2SO_4$, methanesulfonic acid, p-toluenesulfonic acid, immobilized acids (fixed on polymeric carriers) e.g. like Amberlyst™, preferably concentrated $H_2SO_4$. Dependent on the used acid, the reaction can be performed at temperatures from 10° C. to 150° C. A preferred temperature range for the use of concentrated $H_2SO_4$ as solvent is from 10 to 25° C. For concentrated $H_2SO_4$, the weight ratio of starting material to the concentrated $H_2SO_4$ is from 1:0.2 to 1:10, preferably 1:1 or less in which case a solvent is required and the preferred temperature range is 70-90° C. The compound of formula VI is added to the acid in solid form or the acid is added to a solution of compound of formula VI in an organic solvent. The reaction can be supported by azeotropic distillation of water, optionally under reduced pressure, especially if a catalytic amount of acid is used.

Suitable organic solvents for reaction step d) are for example toluene, xylene, methyl cyclohexane chlorobenzene or dichlorobenzene, preferably toluene. As any elimination, this reaction can be done by converting the hydroxyl to a suitable leaving group such as for example halogen (Br, Cl, by reaction for example with $PCl_5$, $PBr_3$, $SOCl_2$) or sulfonate (by reaction for example with methansulfonylchloride in presence of base) followed by treatment with a base, acid or lewis acid (for example KOH, NaOH NaO$^t$Bu, KO$^t$Bu or tertiary amines including aromatic such as for example pyridine).

The compound of formula VII can occur in the following isomers or mixtures thereof:

(VIIa)

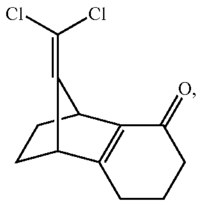

(VIIb)

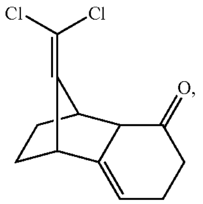

(VIIc)

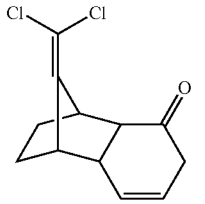

and (VIId)

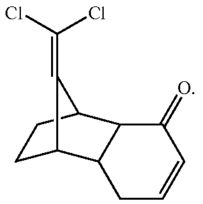

The isolation or purification of a specific isomer or a isomer mixture of formula VII is not necessary. The compound of formula VII and its isomers are novel and especially developed for the process according to the invention and therefore constitute a further object of the invention.

Reaction Step e):

Hydroxylamine can be used as free base in water (50% solution is commercially available) or generated in situ from its salts such as for example hydrochloride or sulfate by treatment with a base (for example triethylamine, pyridine, NaOH or KOH, sodium acetate, potassium or sodium carbonate). Hydroxylamine is preferably used in form of its sulfate or hydrochloride and in an amount of 1 to 2 equivalents, in particular 1.1 to 1.3 equivalents with regard to the compound of formula VII. Suitable bases for this reaction step are for example pyridine, tertiary amines like triethylamine, NaOH or KOH, sodium acetate, potassium or sodium carbonate Especially preferred is sodium acetate and NaOH. The base is used in an amount of 1 to 2 equivalents, preferably 1-1.5 equivalents with regard to the compound of formula VII. Suitable solvents are alcohols (preferred anhydrous), dimethylformamide, N-methyl-2-pyrrolidone, or $CH_3CN$, in particular anhydrous ethanol or anhydrous methanol. An especially preferred solvent is anhydrous ethanol. Reaction step e) can be advantageously performed at temperatures of from 10 to 40° C. preferably at 25° C. or ambient temperature. The reaction can be also performed in a two phase system (organic solvent/water, organic solvent for example are: toluene, xylene, methylcyclohexane) at temperatures of from 50-100° C. using the above mentioned hydroxylamine sources and bases in the presence of phase transfer catalysts selected from carboxylic acids (for example acetic, propionic, isobutyric, pivalic, valeric, isovaleric, benzoic, 2-ethylhexanoic) used in amount 2-50 mol %. A preferred amount of catalyst is 5-10 mol %, a preferred temperature is 80-90° C., preferred catalysts are benzoic acid and 2-ethylhexanoic acid.

With sodium acetate as base, a phase transfer catalyst is not required. This is a preferred embodiment of the process.

The compound of formula VIII can occur in the following isomers or mixtures thereof:

(VIIIa)

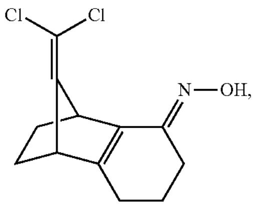

(VIIIb)

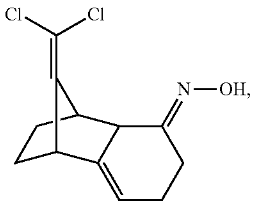

(VIIIc)

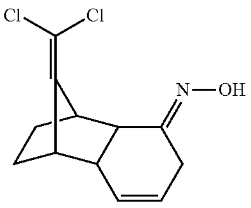

and (VIIId)

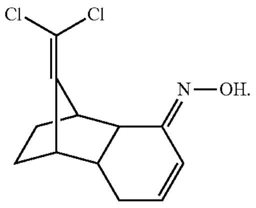

The isolation or purification of a specific isomer or a isomer mixture of formula VIII is not necessary. The compound of formula VIII and its isomers are novel and especially developed for the process according to the invention and therefore constitute a further object of the invention.

Reaction Step f):

The compound of formula IX is known and commercially available. The compound is disclosed, for example, in U.S. Pat. No. 5,093,347.

This step consists of two chemical transformations: reaction of the oxime oxygen with an acid chloride (for example acetyl chloride, pivaloyl chloride, benzoyl chloride or chloroacetyl chloride) or acyl anhydride like acetic anhydride, preferably pivaloyl chloride followed by in situ transformation of the acylated derivative to the compound of formula I by reaction with 1 equivalent of the compound of formula IX advantageously in the presence of an acid (typically HCl or $MeSO_3H$, most preferred HCl). An additional equivalent of the compound of formula IX can be used for the first acylation step (oxime acylation). The use of only one type of acylation reagent is advantageous for the recycling procedure. The acylation is advantageously performed in the presence of a base. The base is used in an amount of 1 to 1.5 equivalents with respect to the compound of formula IX, in particular in equimolar amounts. Suitable bases for reaction step f) are pyridine or tertiary amines like triethylamine. Triethylamine is especially preferred as a base. Preferred reaction temperatures for reaction step f) are from 60 to 120° C., in particular 80-100° C., most preferably 85-95° C. Suitable solvents are toluene, dioxane, tetrahydrofurane, xylene, chlorobenzene or acetonitrile. Most preferred solvent is dioxane.

Reaction step ff) is an especially preferred variant of the process according to the invention: the compound of formula VIII is reacted directly with an excess of the compound of formula IX. The compound of formula IX is used in an excess, preferably in an amount of 2 to 3 equivalents, preferably 2.1 equivalents in relation to the compound of formula VIII. The use of additional acylating agents is not necessary for this variant. The 3-difluoromethyl-1-methyl-1H-pyrazole-4-carboxylic acid formed as by-product in this process variant can be recovered and transformed to the compound of formula IX. Since no additional acylating agents are necessary to perform the reaction, this process variant is economically very advantageous. This process variant does not require the presence of an acid. Further, the reaction can also be performed without a base with a slight reduction of the yield (3-5%).

A preferred process variant comprises f) acylating the oxime oxygen of the compound of formula VIII in the presence of a solvent and an acylating agent and finally reacting the obtained product with a compound of formula IX.

Another preferred process variant comprises ff) reacting the compound of formula VIII with an excess of 2 to 3 equivalents of the compound of formula IX.

In a particular preferred variant of the process of the invention reaction step a) is performed in the presence of $SnCl_4$, $AlCl_3$ or $FeCl_3$ as catalyst;

Pd/C, Pt/C, Rh/C or Raney-Nickel is used as metal catalyst for reaction step b);

$NaBH_4$, monoacetoxyborohydride ($NaBH_3OAc$), $LiAlH_4$, sodium bis(2-methoxyethoxy)aluminum hydride (Red-Al), diisobutylaluminium hydride (DIBAL-H) or borane ($BH_3$*$SMe_2$, $BH_3$*tetrahydrofurane) is used as reducing agent in reaction step c);

phosphoric acid, polyphosphoric acids, concentrated $H_2SO_4$, methanesulfonic acid or p-toluenesulfonic acid is used as the acid in reaction step d);

hydroxylamine is used in form of its hydrochloride in reaction step e); and in step ff) the compound of formula VIII is reacted directly with an excess of 2 to 3 equivalents of the compound of formula IX.

Reaction step a) of this preferred variant of the process is preferably performed with $AlCl_3$ or $FeCl_3$ as the catalyst and in the presence of a donor ligand selected from diethylether, tetrahydrofurane, bis(2-methoxyethyl)ether, nitromethane, nitrobenzene and pyridine.

In an especially preferred variant of the process of the invention reaction step a) is performed in the presence of $AlCl_3$ as catalyst;

Rh/C is used as metal catalyst for reaction step b);

$NaBH_4$ is used as reducing agent in reaction step c);

concentrated $H_2SO_4$ is used as the acid in reaction step d);

hydroxylamine is used in form of its hydrochloride in reaction step e);

and the compound of formula VIII is reacted directly in reaction step ff) with an excess of 2 to 3 equivalents of the compound of formula IX.

The compound of formula VI is novel and represents a further object of the invention. The compound of formula VI can be converted to the compound of formula X, which can be reacted to the compound of formula XI. This is shown in the following reaction scheme 1.

Reaction scheme 1:

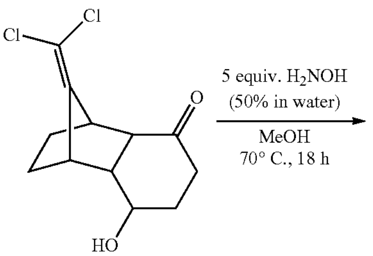

(VI)

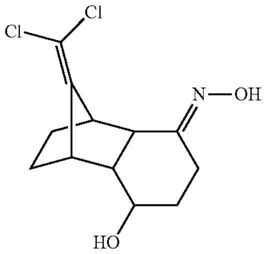

(X)

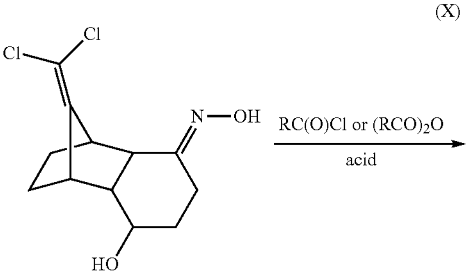

(X)

-continued

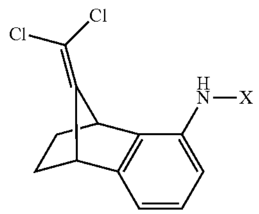

(XI)

X = H, C(O)R

In scheme 1, R is methyl, tert.-butyl, $CH_2Cl$ or phenyl. The compound of formula XI, wherein X is hydrogen, can also be prepared starting from the compound of formula VIII as shown in scheme 2:

Scheme 2:

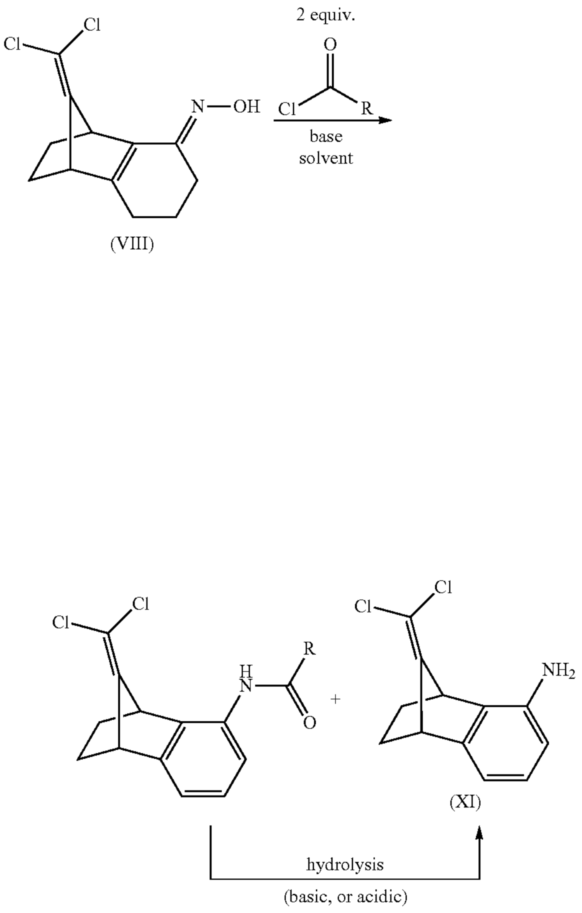

(VIII)

(XI)

In scheme 2, R is methyl, tert.-butyl, $CH_2Cl$ or phenyl. The compound of formula XI is a valuable intermediate for the preparation of the compound of formula I. The compound of formula I can be prepared by the reaction of the compound of formula XI with the compound of formula IX. The compound XI can be also prepared directly (one step) from the compound VIII by heating VIII in the presence of an acid (HCl) in suitable solvent (for example dioxane). Also this transformation can be done by heating VIII in the presence of a catalytic amount of Pd/C (0.5-5 mol %) in high boiling solvent such as triglyme at 180° C.

PREPARATORY EXAMPLES

Example P1

Preparation of the Compound of Formula IV

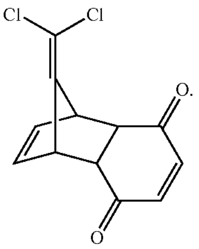

(IV)

Catalyst Solution:

To a stirred suspension of $AlCl_3$ (60.0 g, 0.45 mol) in toluene (200 g) was added tetrahydrofurane (46.0 g, 0.64 mol) dropwise at 20-25° C. under inert atmosphere (nitrogen). The clear solution of catalyst was stored at room temperature.

Diels-Alder Cycloaddition:

A glass reactor was loaded with a cold solution of 6,6-dichlorofulvene in toluene (858 g, 0.479 mol, 8.2%) and 1,4-benzoquinone (56.9 g, 0.526 mol). The reactor content was cooled to −9° C. while being stirred under inert atmosphere (nitrogen). Catalyst solution (40 g, contains 7.8 g $AlCl_3$) was added into the reactor withing 30 min at −9° C., then an additional amount of catalyst solution (10 g, contains 2.0 g $AlCl_3$) was added withing 60 min. After stirring for 3.5 hours at −9° C., the reaction mixture was quenched by dropwise addition of ethanol (70 ml) at −9° C. The reaction mass was stirred at −9° C. for 30 min and filtered. The product was washed with cold ethano/toluene mixture (2:1, 360 ml) and dried in vacuum. Yield 102 g (83%).

$^1H$ NMR ($CDCl_3$, 400 MHz) δ 3.40 (m, 2H), 4.09 (m, 2H), 6.21 (t, J=2.0 Hz, 2H), 6.66 (s, 2H). $^{13}C$ NMR ($CDCl_3$, 75 MHz) δ 47.5, 49.6, 103.4, 134.8, 142.6, 147.6, 196.6.

Example P2

Preparation of the Compound of Formula V

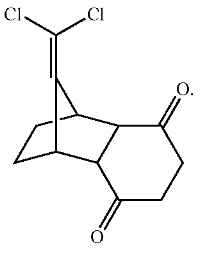

(V)

1 L two-neck flask was charged with compound of formula IV (36.6 g, 0.143 mol) and 5%-Rh/C (3.0 g, 0.42 mol % Rh, water content 58.0%). The flask was evacuated and refilled with nitrogen two times followed by addition of tetrahydrofurane (600 ml). Then the reaction mixture was evacuated until tetrahydrofurane boils and refilled with hydrogen from a balloon two times. Consumption of hydrogen was monitored using a bubble counter. Intensive stirring of the reaction mixture is essential for fast hydrogenation. The conversion was monitored by $^1$H NMR and was complete after 7 hours. At this time consumption of hydrogen became very slow. The reaction mixture was filtered through a glass frit filter. The filter cake, which contained undissolved product, was washed with tetrahydrofurane few times to dissolve it. The combined filtrate was evaporated and the remaining crystalline residue was stirred with methanol (150 ml) for about 15 min at ambient temperature, then cooled in an ice bath, stirred for additional 15 min, filtered, washed with methanol and dried in air. Yield 32.7 g (88%).

$^1$H NMR ($CDCl_3$, 400 MHz) δ 1.47-1.53 (m, 2H), 1.72-1.79 (m, 2H), 2.51-2.60 (m, 2H), 2.82-2.92 (m, 2H), 3.20 (m, 2H), 3.37 (m, 2H). $^{13}$C NMR ($CDCl_3$, 100 MHz) δ 23.7, 38.8, 43.9, 50.5, 106.9, 144.0, 207.8.

Example P3

Preparation of the Compound of Formula VI (VI)

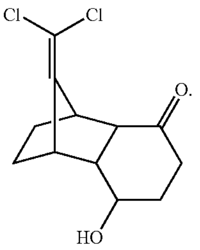

A mixture of the compound of formula V (47.3 g, 0.183 mol), methanol (300 ml) and tetrahydrofureane (300 ml) was cooled to 0-5° C. in an ice bath. Sodium borohydride (2.17 g, 0.0573 mol) was added in portions during 1.5 hours. The reaction mixture was allowed to warm to ambient temperature and the solvent was removed by rotary evaporation. The residue was partitioned between methyl-tert-butylether (1000 ml) and 0.5N HCl (300 ml). The organic phase was separated, filtered and evaporated. The residue was dried in vacuum. Yield 46.9 g (98%, 9:1 mixture of isomers at the hydroxyl).

$^1$H NMR ($CDCl_3$, 400 MHz) δ (major isomer) 1.58-1.72 (m, 3H), 1.84 (bs, 1H), 2.04 (m, 2H), 2.20-2.35 (m, 2H), 2.48-2.55 (m, 1H), 2.74 (m, 2H), 3.12 (m, 1H), 3.28 (m, 1H), 4.41 (m, 1H).

Example P4

Preparation of the Compound of Formula VII (VII)

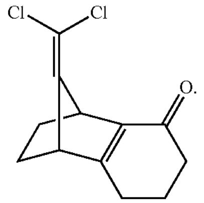

Finely powdered compound of formula VI (26.25 g, 0.1005 mol) was added within 10 min to an intensively stirred 96% sulphuric acid (80 ml) at ambient temperature (cooling with a water bath). The reaction mixture was stirred at the same temperature for 30 min and then poured slowly into a mixture of ice (200 g), ice-cold water (200 ml) and methyl-tert-butylether (250 ml) under vigorous stirring. The organic phase was separated and the water phase was extracted with methyl-tert-butylether (70 ml). The combined extract was washed with 3% solution of sodium bicarbonate (150 ml) and then with brine (100 ml). The organic phase was separated and the solvent was removed by rotary evaporation. The residue was extracted into boiling hexane (100+10+10 ml). The hot solution was filtered through a glass frit filter (slight evacuation) and left for crystallization at ambient temperature. After 1 hour the crystallization mixture was further cooled to 0° C. (ice bath) and kept at this temperature for 30 min. The large crystals formed were filtered, washed with hexane (30 ml) and dried in air. The mother liquor was concentrated to 15 ml volume and additional crop was collected. Yield 20.7 g (85%).

$^1$H NMR ($CDCl_3$, 400 MHz) δ (major isomer) 1.23-1.32 (m, 2H), 1.88-2.14 (m, 4H), 2.23-2.30 (m, 1H), 2.35-2.57 (m, 3H), 3.49 (m, 1H), 3.87 (m, 1H). $^{13}$C NMR ($CDCl_3$, 100 MHz) δ 23.3, 24.2, 25.0, 25.7, 37.4, 42.2, 49.6, 102.3, 140.7, 149.2, 167.1, 193.7.

Example P5-a

Preparation of the Compound of Formula VIII (VIII)

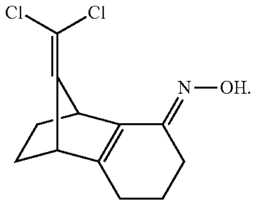

A mixture of compound of formula VII (24.6 g, 0.101 mol), hydroxylamine hydrochloride (8.43 g, 0.121 mol), pyridine (12.0 g, 0.152 mol) and absolute ethanol was stirred at ambient temperature for 4 hours. The reaction mixture was partitioned between ethyl acetate (500 ml) and water (500 ml). The organic phase was separated, washed two times with water (500 ml) and evaporated. The remaining crystalline residue was dried in vacuum. Yield 25.6 g (99%).

$^1$H NMR (DMSO-d6, 400 MHz) δ (major isomer) 1.17 (m, 1H), 1.32 (m, 1H), 1.67 (m, 2H), 1.77-1.92 (m, 2H), 2.14-2.31 (m, 3H), 2.50 (m, 1H), 3.36 (d, J=3.4 Hz, 1H), 3.64 (d, J=3.3 Hz, 1H), 10.70 (s, 1H).

Example P5-b

Preparation of the Compound of Formula VIII (in Two Phase System)

In a glass reactor a mixture of compound VII (30.0 g, 0.123 mol), hydroxylamine sulfate (12.15 g, 0.074 mol), sodium acetate (12.15 g, 0.148 mol), toluene (100 ml) and water 15 ml was stirred at 85° C. for 3 hours. Water (30 ml) was added to the reaction mixture followed by dropwise addition of aqueous sodium hydroxide solution (18.1 g, 0.136 mol, 30%) while maintaining the temperature in 80-85° C. range. The water phase was separated (hot) and the organic phase was partially evaporated (65 ml of toluene was removed). The resulting suspension was cooled to −10° C., stirred at this temperature for an hour and filtered. The product was washed with cold toluene (20 mL) and dried in vacuum at 60° C. Yield 29.6 g (92%, 99%-pure product).

Example P6

Preparation of the Compound of Formula I (Reaction Step f)

(I)

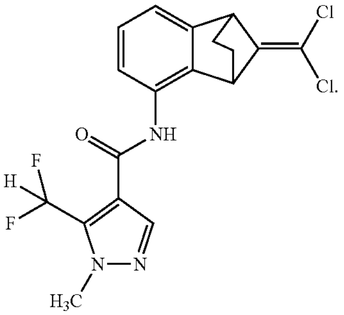

A mixture of compound of formula VIII (5.16 g, 0.02 mol), pivaloyl chloride (2.41 g, 0.02 mol), triethylamine (2.04 g, 0.02 mol) and dioxane (80 ml) was stirred at 40° C. for 30 min. Then a solution of HCl in dioxane (2 ml, 0.01 mol, 2.0M) and DFPA-Cl (compound of formula IX) (3.89 g, 0.02 mol) were added. The reaction mixture was heated at 85° C. for 1.5 hours. After cooling to ambient temperature, a major part of the solvent was removed by rotary evaporation and the residue was partitioned between ethyl acetate (100 ml) and water (100 ml). The organic phase was separated, washed with 1N NaOH (100 ml) then two times with water (100 ml) and evaporated. The remaining residue was dried in vacuum. Yield 6.60 g (70%, 85% pure by quantitative $^1$H NMR).

The crude material (5.00 g) was dissolved in a mixture of xylene (10 ml) and methylcyclohexane (5 ml) at 80° C. The solution was cooled slowly with agitation to 5° C. (ice bath). The precipitate was filtered, washed with cold xylene (1 g) and dried in vacuo. Yield 3.0 g (50%, 99+% pure by quantitative $^1$H NMR).

$^1$H NMR ($CDCl_3$, 400 MHz) δ 1.37 (m, 1H), 1.49 (m, 1H), 2.09 (m, 2H), 3.90 (s, 3H), 3.94 (m, 1H), 4.07 (m, 1H), 6.91 (t, $J_{H-F}$=54.2 Hz, 1H), 7.02 (d, J=7.3 Hz, 1H), 7.16 (t, J=7.8 Hz, 1H), 7.79 (d, J=8.2 Hz, 1H), 8.01 (s, 1H), 8.15 (m, 1H).

Example P7

Preparation of the Compound of Formula I (Reaction Step ff)

To a stirred solution of the compound of formula VIII (5.00 g, 0.0193 mol) and triethylamine (1.76 g, 0.0174 mol) in dioxane (25 ml) was added the compound of formula IX (7.91 g, 0.0406 mmol) during a 15 min period while keeping the temperature in a 25-35° C. range. The reaction mixture was heated slowly to a temperature of 82° and kept at this temperature for 3 h. After cooling to ambient temperature most of the solvent was removed by rotary evaporation and the residue was stirred with methyl-tert-butylether (150 ml) and water (35 ml) for 25 min. A solution of NaOH (2.4 g, 0.06 mol) in water (10 ml) was added and the mixture was stirred for additional 30 min. The water phase was separated and the organic phase was extracted with 1N NaOH (5 ml). The combined water extracts was acidified with 32% HCl (5 ml, 0.05 mol), cooled to 0° C. and the resulting suspension was stirred at this temperature for 30 min. The white precipitate was filtered, washed with water (20 mL) and dried to give 99%-pure DFPA-acid. Yield 3.60 g (96%).

The organic phase was washed with 1N HCl (50 ml, 0.05 mol) and then with water (50 ml). The solvent was slowly removed by rotary evaporation and the remaining crystalline residue was dried in vacuum at 50° C. Yield 7.66 g (96%, 95% purity).

This material was stirred with methylcyclohexane (50 ml) at reflux for 30 min. The suspension was cooled slowly to 45° C. The crystalline material was filtered, washed with methylcyclohexane and dried in air to give pure compound of formula I. Yield 7.07 g (92%, 99% pure according to quantitative $^1$H NMR).

Depending on the purity of the compound of formula IX, the final product can contain small amounts of byproducts of formula $B_1$ and $B_2$:

($B_1$)

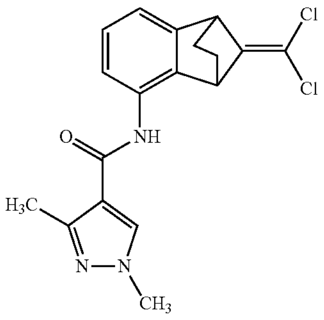

and

-continued (B2)

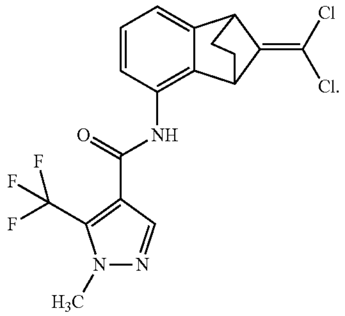

What is claimed is:

1. A process for the preparation of the compound of formula I (I)

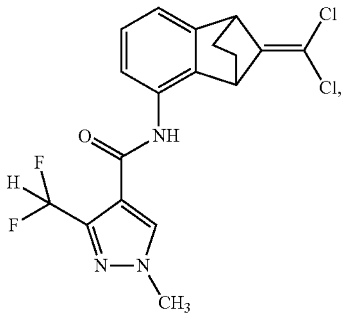

which process comprises a) reacting the compound of formula II (II)

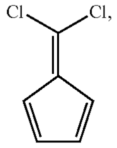

in the presence of a catalyst in a suitable organic solvent with the compound of formula III (III)

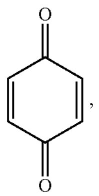

to the compound of formula IV (IV)

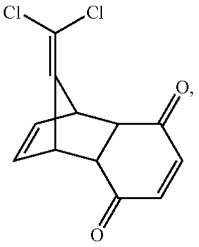

b) hydrogenating the compound of formula IV in the presence of a metal catalyst to the compound of formula V (V)

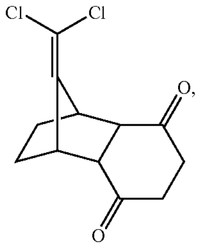

c) reducing the compound of formula V in the presence of a reducing agent to the compound of formula VI (VI)

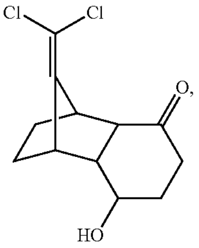

d) dehydrating the compound of formula VI in the presence of an acid to the compound of formula VII (VII)

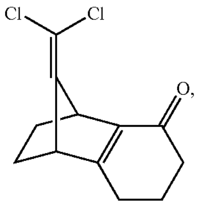

e) reacting the compound of formula VII with hydroxylamine to the compound of formula VIII

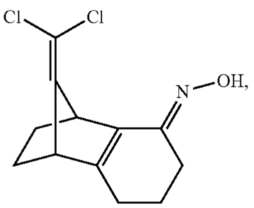

(VIII)

and f) acylating the oxime oxygen of the compound of formula VIII in the presence of a solvent and an acylating agent and finally reacting the obtained product with the compound of formula IX

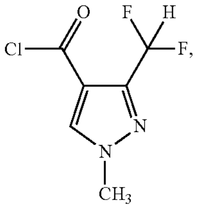

(IX)

or ff) reacting the compound of formula VIII with an excess of the compound of formula IX.

2. A process according to claim 1, which process comprises f) acylating the oxime oxygen of the compound of formula VIII in the presence of a solvent and an acylating agent and finally reacting the obtained product with a compound of formula IX.

3. A process according to claim 1, which process comprises if) reacting the compound of formula VIII with an excess of 2 to 3 equivalents of the compound of formula IX.

4. The compound of formula IV

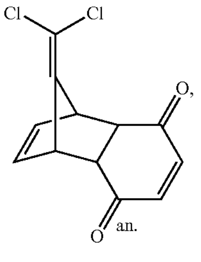

(IV)

and its stereoisomers.

5. The compound of formula V

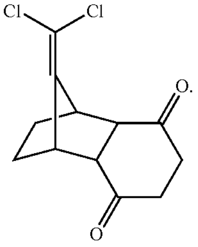

(V)

and its stereoisomers.

6. The compound of formula VI

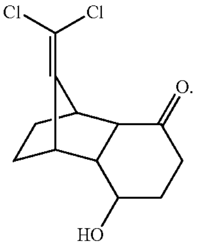

(VI)

and its stereoisomers.

7. The compound of formula VII

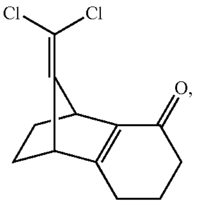

(VII)

and its stereoisomers.

8. The compound of formula VIII

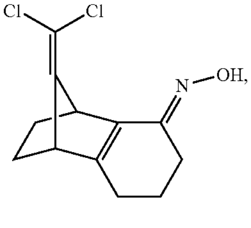

(VIII)

and its stereoisomers.

* * * * *